(12) United States Patent
Assie et al.

(10) Patent No.: US 7,650,995 B2
(45) Date of Patent: *Jan. 26, 2010

(54) DISPOSABLE PHARMACEUTICAL OR COSMETIC PRODUCT APPLICATOR

(75) Inventors: Jean-Louis Assie, Bergerac (FR); Bernard Pauchet, Saint Capraise de Lalinde (FR)

(73) Assignee: Taiki Corporation, Ltd., Osaka (JP)

( * ) Notice: Subject to any disclaimer, the term of this patent is extended or adjusted under 35 U.S.C. 154(b) by 410 days.

This patent is subject to a terminal disclaimer.

(21) Appl. No.: 10/532,330

(22) PCT Filed: Oct. 30, 2003

(86) PCT No.: PCT/FR03/03239

§ 371 (c)(1),
(2), (4) Date: Apr. 22, 2005

(87) PCT Pub. No.: WO2004/041137

PCT Pub. Date: May 21, 2004

(65) Prior Publication Data

US 2006/0155251 A1 Jul. 13, 2006

(30) Foreign Application Priority Data

Oct. 30, 2002 (FR) .................................. 02 13622

(51) Int. Cl.
*A61L 15/00* (2006.01)

(52) U.S. Cl. ........................ 206/440; 206/438; 206/229

(58) Field of Classification Search ................. 206/570, 206/229, 438, 440, 441, 484; 602/48, 57; 401/132, 133, 196
See application file for complete search history.

(56) References Cited

U.S. PATENT DOCUMENTS

| 2,817,336 | A | | 12/1957 | Kravitz et al |
| 3,053,255 | A | | 9/1962 | Meyer |
| 3,580,254 | A | | 5/1971 | Stuart |
| 3,635,567 | A | | 1/1972 | Richardson, Jr. |
| 3,826,259 | A | * | 7/1974 | Bailey ......................... 401/132 |
| 4,372,098 | A | * | 2/1983 | Mason ......................... 53/412 |
| 4,696,393 | A | | 9/1987 | Laipply |
| 4,762,124 | A | * | 8/1988 | Kerch et al. .................. 206/438 |
| 4,808,172 | A | | 2/1989 | Murata |
| 4,858,604 | A | | 8/1989 | Konishi |
| 4,896,768 | A | * | 1/1990 | Anderson .................... 206/210 |
| 4,915,102 | A | * | 4/1990 | Kwiatek et al. .............. 206/440 |

(Continued)

FOREIGN PATENT DOCUMENTS

EP 0 368 408 5/1990

(Continued)

*Primary Examiner*—J. Gregory Pickett
(74) *Attorney, Agent, or Firm*—Richard M. Goldberg

(57) ABSTRACT

Single-use packaging for a dose of liquid, semiliquid, or powder substance, includes a protective cover having two separable parts of leakproof material together with a breakable blister containing the substance and attached to the inside face of one of the two parts.

11 Claims, 2 Drawing Sheets

U.S. PATENT DOCUMENTS

| | | |
|---|---|---|
| 5,271,940 A | 12/1993 | Cleary et al. |
| 5,487,932 A | 1/1996 | Dunshee |
| 5,511,689 A | 4/1996 | Frank |
| 5,562,642 A * | 10/1996 | Smith et al. .................. 401/132 |
| 6,000,403 A | 12/1999 | Cantwell |
| 6,086,912 A | 7/2000 | Gilman |
| 6,446,795 B1 | 9/2002 | Allen et al. |
| 6,547,468 B2 * | 4/2003 | Gruenbacher et al. ....... 401/132 |
| 6,607,514 B2 | 8/2003 | Reese |
| 6,695,515 B1 * | 2/2004 | Fleury ........................ 401/132 |
| 6,823,649 B1 | 11/2004 | Pauchet |
| 7,163,101 B2 | 1/2007 | Harper |
| 7,240,790 B2 * | 7/2007 | Wendel et al. .............. 206/440 |
| 2002/0011424 A1 | 1/2002 | Wilkman |
| 2003/0106812 A1 | 6/2003 | Wilkman |
| 2006/0163101 A1 * | 7/2006 | Assie et al. .................. 206/440 |

FOREIGN PATENT DOCUMENTS

| | | |
|---|---|---|
| EP | 1040824 A2 | 4/2000 |
| FR | 2801179 A1 | 5/2001 |
| WO | WO 94/09735 | 5/1994 |

* cited by examiner

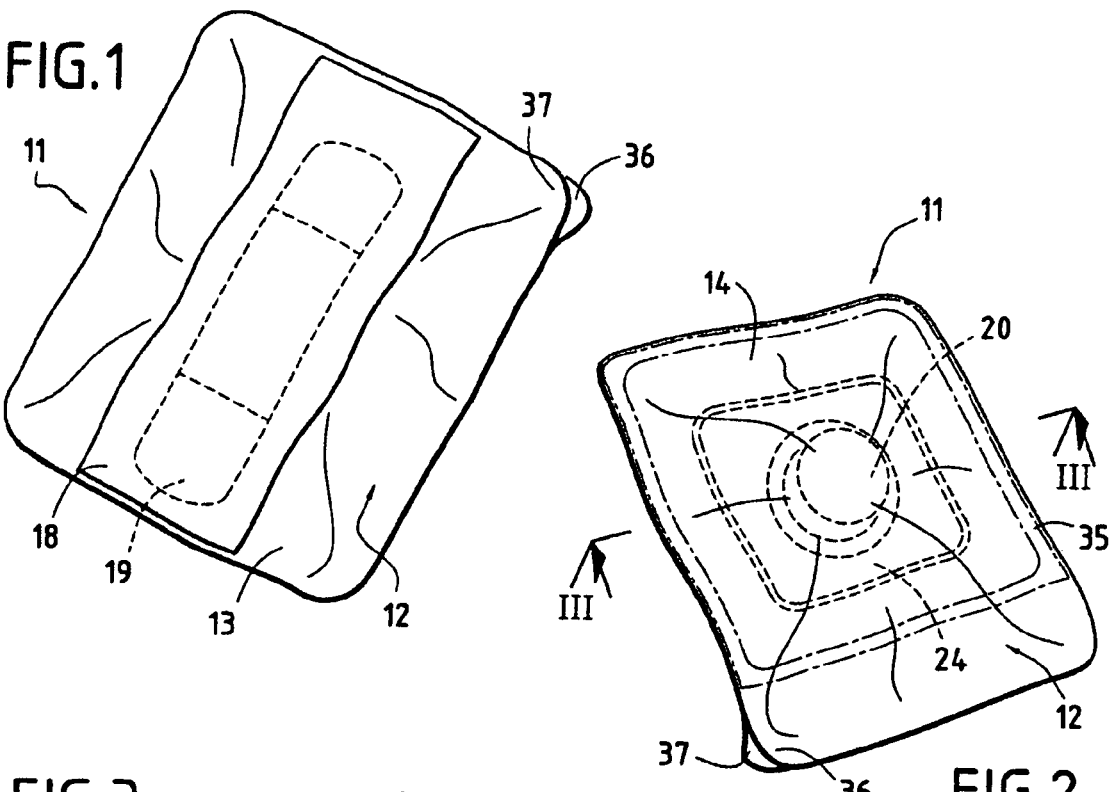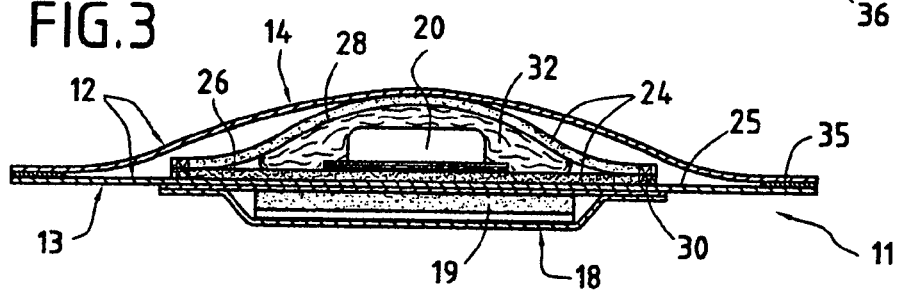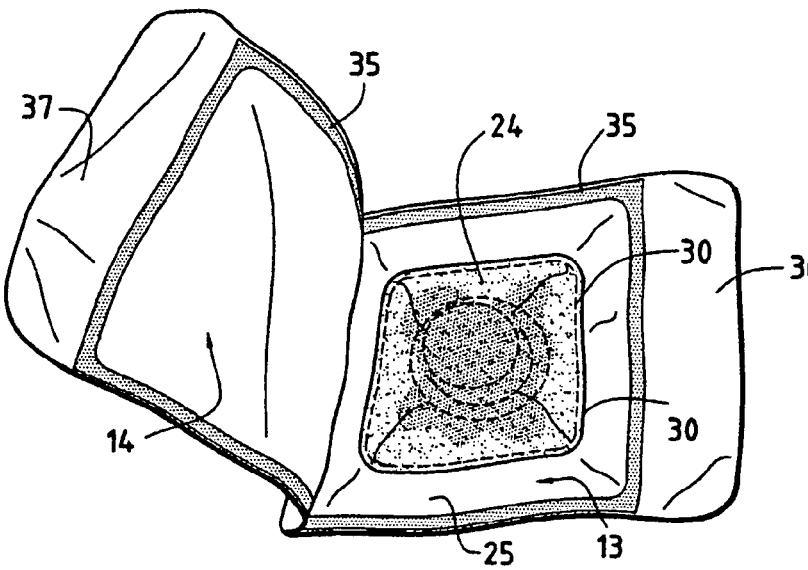

DISPOSABLE PHARMACEUTICAL OR COSMETIC PRODUCT APPLICATOR

BACKGROUND OF THE INVENTION

The present invention relates to single-use packaging for a liquid, semiliquid, or powder substance offered for sale in the form of doses. The preferred field of application of the invention is that of applying cosmetic, medical, or antiseptic compositions, in particular any composition for application to the skin.

When traveling or engaging in sport, it can be desirable to have a cosmetic, medical, or antiseptic substance available that is packaged in the form of one dose for single use, with the packaging being discardable after use.

For example, it is known to enclose such a dose of substance in a small blister having a flexible wall made from two sheets of plastics material that are heat-sealed together around a closed outline. For example, blisters can be made from such sheets in strip form that are united to form a succession of blisters. Doses of substance are injected between the sheets prior to forming the heat seals and the blisters are subsequently separated from one another. Such a method is described by way of example in French patent application FR 99/14729, which also shows how such blisters can be integrated in an applicator-forming pouch. The applicator-forming portion is protected by a leakproof capsule. At the time of use, the pouch is flattened so that the substance wets the applicator thus enabling it to be applied to the skin, or to a wound if the substance is a disinfectant.

SUMMARY OF THE INVENTION

The invention seeks to improve that kind of packaging.

More particularly, the invention provides a single-use packaging for a liquid, semiliquid, or powder substance, the packaging being of the type containing a breakable leakproof blister containing one dose of said substance, the packaging being characterized in that it comprises a protective cover made of two separable parts of leakproof material, and in that said blister is attached to the inside face of one of said two parts.

The first advantage which results from this novel structure is that once the protective cover has been opened it makes application easier and there is no risk of the user covering the fingers with the substance in question.

Preferably, when the blister is housed in a pouch including an applicator, said pouch is fixed to the above-mentioned inside face of one of the two parts. Under such circumstances, the applicator is impregnated with substance when the blister is broken, and this operation can be performed prior to opening the protective cover, by exerting sufficient finger pressure on the cover to break the blister inside the applicator.

If use of the substance does not need an applicator, then the blister can be fixed directly to said inside face.

In a presently preferred embodiment, the cover is made of two flexible and leakproof parts, typically obtained from sheets of plastics and metal materials laminated together. The two parts are united by a closed outline junction line surrounding the location of the pouch. Consequently, when the packaging is offered to the user, the pouch is completely enclosed in the leaktight protective cover while the blister is itself enclosed in the pouch including the applicator. The pouch can be heat-sealed via one of its faces to said inside face of one of the two parts constituting the protective cover.

In an advantageous embodiment, the pouch itself comprises a first part made of flexible material (typically of the non-woven cloth type) which is fixed to said inside face, and a second part made of a material that is flexible and porous, forming said applicator. These two parts are united by a closed outline junction line and they hold said blister captive between them. A piece of cotton wool or the like may be housed in the pouch, preferably between the blister and said second part made of flexible and porous material forming said applicator.

According to another advantageous characteristic, when the above-defined packaging contains a dose of disinfectant or treatment substance, for application to a wound or a burn, the packaging is associated with an adhesive dressing. More precisely, a peel-off cover containing said adhesive dressing is fixed via one of its faces on an outside face of the protective cover. Consequently, after the substance has been applied, the user need not search through other equipment to find an adhesive dressing for protecting a wound, since the dressing is available on the packaging itself. In order to ensure that said dressing can be applied very easily, possibly with one hand only, the outside face of said dressing is weakly secured to the inside face of the portion of the peel-off cover that is not fixed to the protective cover. This type of dressing is known in itself and is described in U.S. Pat. No. 5,511,689, but the fact of disposing it on the packaging makes it easier to use.

BRIEF DESCRIPTION OF THE DRAWINGS

The invention appears more clearly in the light of the following description of a presently preferred embodiment of single-use packaging implementing its principle, described solely by way of example and given with reference to the accompanying drawings, in which:

FIG. 1 is a diagrammatic perspective view of packaging in accordance with the invention;

FIG. 2 is a view of the underside of FIG. 1;

FIG. 3 is a section view on III-III of FIG. 2;

FIG. 4 is a view of the open packaging, ready for use;

DETAILED DESCRIPTION

Figure 5:
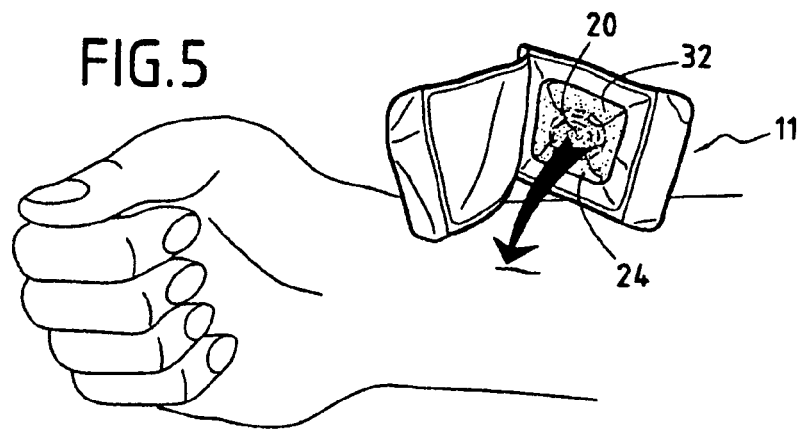
FIG. 5 shows the implementation of the applicator on a wound.

The single-use packaging 11 as offered to the user is externally in the form of a cover 12, referred to below as a "protective cover" made of two separable parts of leakproof material 13, 14. When this applicator is for applying a disinfectant or the like, said protective cover carries another cover 18 on one of its faces, which other cover can be peeled off and retains an adhesive dressing. The features of this peel-off cover and of this dressing are described below. This is merely an option useful when the substance contained in the packaging is for treating a wound or a burn to be subsequently protected by said dressing.

The packaging also contains a leaktight blister 20 that can be broken to release one dose of substance to be applied. This blister is attached to the inside face of one of the two parts making up the protective cover. In other words, the blister 20 cannot be detached from the protective cover 12, even when the cover has been opened. In the example, the blister 20 is housed in a pouch 24 containing an applicator, where this arrangement is known in itself. The pouch 24 is fixed to the inside face 25 of the part 13 of the protective cover. Since the blister 20 is breakable, the applicator is wetted with said substance once the blister has been broken. This operation is performed by applying pressure to the protective cover 12 prior to opening it.

As can be seen in FIG. 3, the pouch 24 comprises a first part made of flexible material 26 which is secured, specifically heat-sealed, to said inside face 25, and a second part of material 28 that is flexible and porous, forming said applicator. In the example described, said first part 26 is taken from sheet material of the non-woven type, while the second part is also taken from a sheet of material of the non-woven type, but which also presents all of the qualities needed for applying the substance. It is preferable to use a non-woven type material that is based on cotton, of the fluffless type. These two parts which are identical as to shape and dimensions are united by a peripheral junction line of closed outline. They hold said blister captive between them. In addition, a piece of cotton wool 32 or the like is housed in the pouch, between the blister 20 and said second part 28. The two parts forming the walls of the pouch are united and the pouch is heat-sealed to the inside face 25 of the part 13 of the protective cover 12 by melting their component materials by applying a hot tool having the shape of the junction outline 30.

The two parts 13, 14 are also made of flexible material and they are united via a junction line 35 of closed outline surrounding the location for the pouch. To make the substance easier to apply, the surface area of each part 13, 14 of the protective cover is subsequently greater than the surface area of the pouch 24 which is fixed in the center of one of said two parts of leakproof material. The junction line 35 thus surrounds an area that is significantly greater than that occupied by the pouch, substantially at the center of said part of leakproof material. This junction line 35 is a line of adhesive or of heat-sealing that is not very strong so as to allow the two above-specified parts to be separated by being peeled apart. Certain laminates of metallized plastics material have been designed to provide such "peelability".

By way of example, the part 13 on which the pouch is fixed may be made from a laminate constituted by a 12 micrometer (μm) thick layer of polyethylene, a layer of metallization, and another layer of polyethylene (PE) that is 80 μm thick, making peeling possible. The other part making up the protective cover may be made out of another, similar laminate. At least one of the two surfaces that are pressed against each other is treated so as to make peeling possible once the closed outline junction line 35 has been made by applying a hot tool of corresponding shape against each of the two parts, and after said pouch has been heat-sealed.

As shown, a fraction of the length of the junction line 35 extends at a distance from the facing edges of said two parts 13, 14 of flexible material, thereby defining two pull tabs 36, 37 for use in separating said two parts. After being included in the protective cover, the pouch 24 (and thus in particular the applicator) are subjected to sterilization treatment by gamma rays.

To apply the substance, the center of the closed protective cover is squeezed so as to break the blister 20. The substance then wets the applicator (see FIG. 4) and it is then possible to open the protective cover 12 via at least three of its sides. The open cover makes the pouch 24 easier to handle and makes it easier to use the substance that has been made available through the applicator (FIG. 5).

Figure 6:
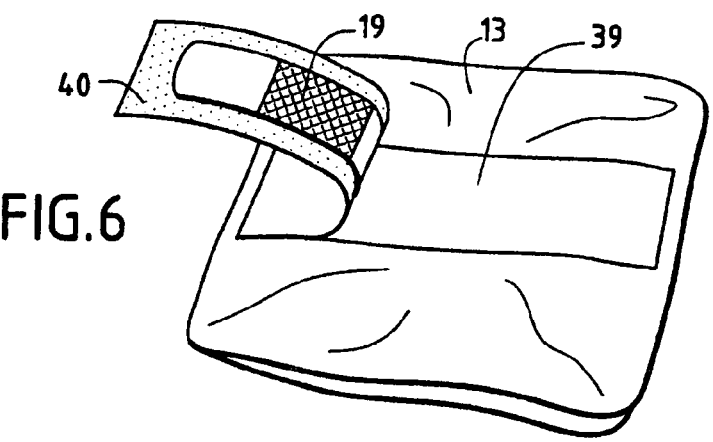
FIGS. 6 to 8 show the use of an adhesive dressing.
Figure 7:
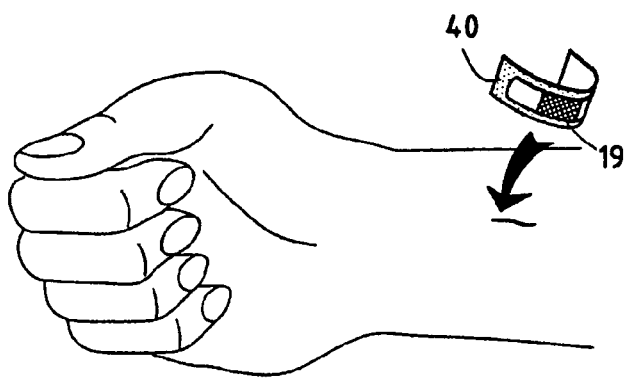
Figure 8:
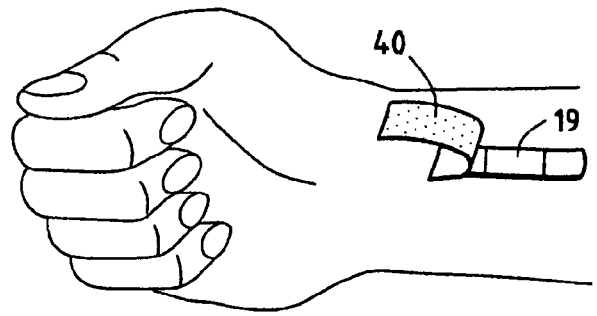

The peel-off cover 18 containing the adhesive dressing 19 is fixed via one of its faces to an outside face of the protective cover 12. The inside portion 39 of the peel-off cover 18 which is fixed to the outside surface of the protective cover presents resistance to being torn off that is subsequently greater than the force needed for opening the peel-off cover. Consequently, the inside portion of the peel-off cover remains attached to said protective cover when the peel-off cover is opened in order to take hold of the dressing (see FIG. 6). However, the outside face of the dressing is weakly secured (e.g. by moderate adhesive) to the inside face of the outside part 40 of the peel-off cover which is not fixed to the protective cover. Consequently, when the peel-off cover is opened, the dressing 19 remains fixed to the part 40 which is pulled. Once the adhesive parts have been separated, the dressing can be applied (FIG. 7) by handling the detached portion of said peel-off cover without any risk of touching the sterilized zone. In contrast, once they have been applied to the skin, the adhesive zones of the dressing stick sufficiently strongly to the skin (FIG. 8) to ensure that when traction is applied to said portion 40 of the peel-off cover, it is said portion that is detached from the dressing. The sterilization treatment may be applied after the peel-off cover containing the dressing has been secured, to said protective cover containing the pouch.

The invention claimed is:

1. Single-use packaging for a liquid, semiliquid, or powder substance, the packaging comprising:
   a protective cover made of two separable parts of leakproof material, and
   a breakable leakproof blister containing one dose of said substance for application to skin of a person, and
   a pouch comprising an applicator, wherein:
   said blister is housed in said pouch with said pouch completely surrounding said blister on all sides thereof,
   said pouch is permanently fixed in operation to an inside face of one of said two separable parts and enclosed in said protective cover,
   said applicator is impregnated with said substance when said blister is broken, and
   a material including cotton wool is housed in said pouch such that said substance is distributed in said material when said blister is broken.

2. Packaging according to claim 1, wherein:
   said pouch comprises a first part of flexible material fixed to said inside face, and a second part of material that is flexible and porous, forming said applicator, and
   said two parts are united by a closed outline junction line with said blister being held captive between said two parts.

3. Packaging according to claim 1, wherein said protective cover is made of two flexible parts that are united by a closed outline junction line surrounding a location of said pouch.

4. Packaging according to claim 3, wherein said junction line surrounds an area that is significantly greater than an area occupied by said pouch, and said pouch is located substantially in the center of the area surrounded by said junction line.

5. Packaging according to claim 3, wherein said junction line permits said two parts to be separated by being peeled apart and is one of:
   a line of low strength adhesive, and heat-sealing.

6. Packaging according to claim 3, wherein said junction line extends over a fraction of a length of said two parts at a distance apart from facing edges of said two flexible material parts, to define pull tabs which enable said two parts to be separated.

7. Packaging according to claim 1, further comprising a peel-off cover containing an adhesive dressing with one of its faces fixed on an outside face of said protective cover.

8. Packaging according to claim 7, wherein an outside face of said dressing is weakly secured to an inside face of a portion of the peel-off cover that is not fixed to the protective cover.

9. Packaging according to claim 1, wherein the applicator has a convex, rounded shape.

10. Single-use packaging for a liquid, semiliquid, or powder substance, the packaging comprising:
- a protective cover made of two separable parts of leakproof material,
- a breakable leakproof blister containing one dose of said substance for application to skin of a person, and
- a pouch comprising an applicator, wherein:
  - said protective cover is made of two flexible parts that are united by a closed outline junction line surrounding a location of said pouch, and
  - said pouch is permanently fixed in operation to an inside face of one of said two separable parts and enclosed in said protective cover,
  - said pouch comprises a first part of flexible material fixed to said inside face, and a second part of material that is flexible and porous, forming said applicator, and
  - said two parts of said pouch are united by a closed outline junction line with said blister being held captive between said two parts with said pouch completely surrounding said blister on all sides thereof, and
  - said junction line of said protective cover surrounds an area that is significantly greater than an area occupied by said pouch, and said pouch is located substantially in a center of an area surrounded by said junction line, and
  - said applicator is impregnated with said substance when said blister is broken, and
  - a material including cotton wool is housed in said pouch such that said substance is distributed in said material when said blister is broken.

11. Single-use packaging for a liquid, semiliquid, or powder substance, the packaging comprising:
- a protective cover made of two separable parts of leakproof material, and
- a breakable leakproof blister containing one dose of said substance for application to skin of a person, and
- a pouch comprising an applicator, wherein:
  - said blister is housed in said pouch with said pouch completely surrounding said blister on all sides thereof,
  - said blister is entirely non-detachably fixed to one of:
    a) said pouch, and
    b) said protective cover,
  - said pouch is permanently fixed in operation to an inside face of one of said two separable parts and enclosed in said protective cover, and
  - said applicator is impregnated with said substance when said blister is broken, and
  - a material including cotton wool is housed in said pouch such that said substance is distributed in said material when said blister is broken.

* * * * *